United States Patent [19]

Brand et al.

[11] 3,932,507

[45] Jan. 13, 1976

[54] PROCESS FOR THE CHLORINATION OF AROMATIC ISOCYANIDE DICHLORIDES

[75] Inventors: William Wayne Brand, Hopewell; David William Reger, Trenton, both of N.J.

[73] Assignee: American Cyanamid Company, Stamford, Conn.

[22] Filed: Apr. 27, 1973

[21] Appl. No.: 355,119

[52] U.S. Cl............................ 260/566 D; 260/566 D
[51] Int. Cl.².................................... C07C 119/00
[58] Field of Search................................ 260/566 D

[56] References Cited
OTHER PUBLICATIONS

Central Patents Index (Derwent Publications Ltd.) Weeks 9, 11 June 1971, Belgian Pat. No. 755,447.

*Primary Examiner*—Gerald A. Schwartz
*Attorney, Agent, or Firm*—H. G. Jackson

[57] ABSTRACT

This invention relates to a novel process for the preparation of 4-chloro-2-alkylphenylisocyanide dichlorides. More particularly, this invention relates to the chlorination of ortho substituted phenylisocyanide dichlorides exclusively in the para-position. The compounds are useful intermediates in the preparation of ixodicidal, insecticidal, ovicidal and chemosterilizing agents.

10 Claims, No Drawings

PROCESS FOR THE CHLORINATION OF AROMATIC ISOCYANIDE DICHLORIDES

BACKGROUND OF THE INVENTION

It is known that primary aromatic amines and their derivatives can be converted to arylisocyanide dichlorides in good yield by a number of methods, as for example the reactions graphically illustrated by the following equations taught by: E. Kuhle, B. Anders, and G. Zumach, Angewandte Chemie (International Edition), 6, 649 (1967); and J. E. Baldwin and J. E. Patriok, Chemical Communications, 968 (1968).

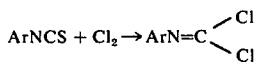

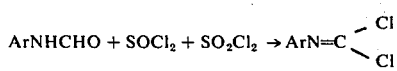

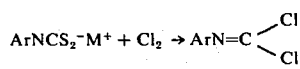

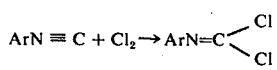

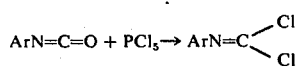

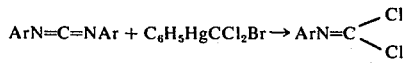

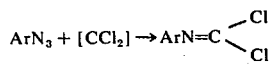

In these equations the legend "Ar" means aryl.

Although such reactions are effective for preparing arylisocyanide dichlorides from primary aromatic amines and derivatives thereof, they do not suggest a means for selectively or exclusively chlorinating phenylisocyanide dichlorides in the para-position. In fact to the contrary, the art reporting the above reactions actually indicates that these reactions yield (a) isomeric mixtures of haloarylisocyanide dichlorides, or (b) fail to achieve ring chlorination at all.

J. V. Nef, Ann. (Justus Liebigs), 270, 267 (1892), reported that chlorination of phenyl isothiocyanate at 0°C. in chloroform solution yielded a mixture of phenylcarbonimidoyl dichloride and the p-chloro derivative thereof. Bly, Perkins and Lewis, J. Am. Chem. Soc., 44, 2896 (1922), attempted chlorination of phenylisothiocyanate in carbon tetrachloride and in phenylcarbonimidoyl dichloride but found no evidence of ring chlorination in either solvent system. D. B. Murphy, J. Org. Chem., 29, 1613, (1964), reported that when chlorination of phenylisothiocyanate is carried out in chloroform using excess chlorine a mixture of p-chlorophenyl carbonimidoyl dichloride, the unsubstituted compound and 2,4-dichlorophenyl carbonimidoyl dichloride, is obtained. Murphy also reported that when excess chlorine was removed from the reaction mixture immediately after the initial chlorination was completed, no ring chlorination occurred. In addition, we have found that chlorination of o-formotoluidide with a chlorine source such as sulfuryl chloride or chlorine gas leads to a mixture of approximately 75% 4-chloro- and 25% 6-chloro-o-formotoluidide. Similar results are also obtained with the acetyl derivative. Since these procedures give isomer mixtures, the additional undesirable step of isomer separation is required.

It was therefore an object of the present invention to find a process which would provide a means for chlorination of o-alkylaniline derivatives exclusively in the para-position.

SUMMARY OF THE INVENTION

The invention relates to a novel process for the manufacture of compounds having the formula:

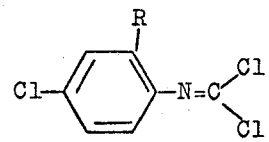

wherein R represents alkyl $C_1$–$C_6$, including straight and branched chain alkyl and cycloalkyl. The invention also relates to a novel process for the chlorination of o-alkyl-phenylisocyanide dichlorides exclusively in the para-position.

We have now discovered that if the chlorination is carried out on an o-alkylphenylisocyanide dichloride, which may be prepared by any of the above or other methods, the chlorine is introduced essentially in the para-position. The chlorination can be carried out with any chlorine source, for example, sulfuryl chloride or chlorine gas. The reaction is normally run at temperatures between 20°–150°C., preferably at 60°–120°C., and can be conducted in the absence of solvents or in a chlorinated hydrocarbon solvent such as chloroform, dichloroethane, methylene chloride or carbon tetrachloride. The reaction may also be carried out in a solvent such as thionyl chloride. Graphically, the reaction may be illustrated as follows:

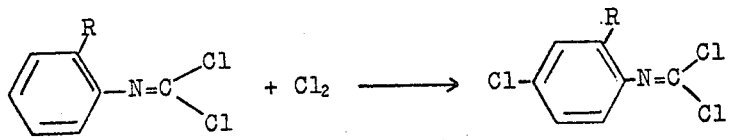

wherein R is alkyl $C_1$–$C_6$. We have also discovered a process for isolation of 4-chloro-2-alkylphenylisocyanide dichlorides. The reaction mixture is stripped of solvent and then diluted with an inert chlorinated hydrocarbon solvent such as methylene chloride, chloroform, dichloroethane or carbon tetrachloride. The resulting solution is then washed with water, dried, and stripped of solvent to give the purified product. The compounds are useful intermediates in the preparation of ixodicidal, insecticidal, ovicidal and chemosterilizing agents.

DETAILED DESCRIPTION

The 2-substituted para-chlorophenylisocyanide dichloride is an especially desirable product since it is an An alternative procedure involves the sequential addition to a solution of suspension of the sulfide (plus base where required), of the isocyanide dichloride, followed by methylene bromide. Alternatively, the sulfide plus base may also be added to a solution of the isocyanide dichloride, followed by addition of methylene bromide. The same requirements on stoichiometry, reaction temperatures, reagents, and solvents apply to this modification as specified for the above procedure.

The present invention is further illustrated by the examples provided below which are not to be construed as limitative.

EXAMPLE 1

4-Chloro-o-tolylisocyanide Dichloride

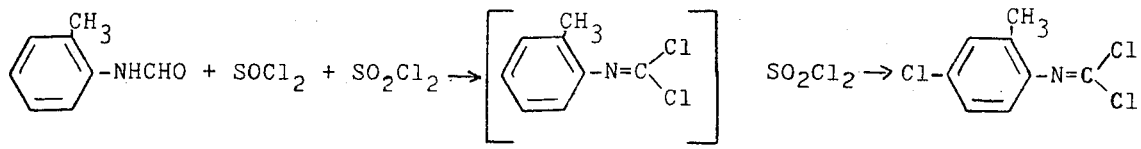

intermediate useful in the preparation of the highly effective ixodicidal, insecticidal, ovicidal and chemosterilizing, 2-alkyl-(4'-chlorophenylimino)-1,3-dithiethanes used for the control of insects and ixodides.

The process is particularly advantageous since it yields the 2-alkyl-4-chlorophenylisocyanide dichloride as a product virtually free of isomeric contamination and readily convertible to the desired 2-substituted (p-chlorophenyl-imino)-1,3-dithietane. These latter-named dithietanes may be prepared by a one-step procedure from phenylisocyanide di-chlorides, thereby eliminating the necessity of isolation and purification of intermediates. One such procedure involves the addition of a sulfide source represented by the formula $H_{a'}SM_{(2-a')}$, wherein $a'$ is an integer 0, 1 or 2; M is an alkali metal, ammonium or primary-secondary- or tertiary-alkyl($C_1$–$C_4$) -ammonium group such as aqueous $(NH_4)_2S$; $Na_2S$, KSH or $H_2S$, to a solution of methylene bromide, an appropriate base, where needed, and the isocyanide dichloride. If $a'=0$ in the sulfide, no additional base is needed; if $a'=1$, one equivalent of base is needed per equivalent of sulfide; and if $a'=2$, two equivalents of base are needed per equivalent of sulfide. Any common base can be used, as for example alkali metal hydroxides, alkali metal bicarbonates, alkali metal carbonates, or perferably tertiary-alkyl(-$C_1$–$C_4$)-amines. Preferably used are 2 to 3 equivalents of methylene bromide to each equivalent of the isocyanide dichloride. The reaction can be run at temperatures between 0°C. and 60°C., and preferably at 20°C. to 40°C. The solvent used can be any polar aprotic solvent or aqueous mixture of an organic solvent which is inert to the reactants such as water, pyridine, sulfolane, ethylene glycol dimethyl ether, diethylene glycol dimethyl ether, esters of lower alkanols, or an aqueous mixture of one of these, or preferable acetonitrile, aqueous acetonitrile, dimethyl sulfoxide (DMSO) aqueous DMSO, dimethylformamide (DMF), aqueous DMF, lower alkyl $C_1$–$C_4$ ketones, or aqueous lower alkyl $C_1$–$C_4$ ketones.

To a solution of 67.5 g. (0.5 mole) of o-formo-toluidide in 450 ml (6.2 mole) of thionyl chloride was added over ½ hr. 162 ml. (2 mole) of sulfuryl chloride. The reaction mixture was stirred at room temperature overnight. It was then heated at reflux for 2¼ hr., after which another 30 ml. (0.375 mole) of sulfuryl chloride was added dropwise over 15 minutes as reflux was continued. After another 1½ hr. of reflux, the reaction could be seen by gas chromatography (140°, 4 ft. SE-30 on Gaschrome Q, 100-120 mesh) to be essentially complete. The solvent was evaporated to afford a crude reaction product contaminated with small amounts of thionyl chloride and sulfuryl chloride. This solution was diluted with 250 ml. of methylene chloride and then was shaken with two 100 ml. portions of water. The organic layer was dried over anhydrous magnesium sulfate, filtered, and stripped of solvent to afford a high yield of product which gas chromatography showed to contain about 9% o-chloro product and 91% p-chloro product. Gas chromatographic examination of aliquots removed during the reaction showed that 6-chloro-o-tolylisocyanide dichloride was present soon after the reaction was begun to the extent of 9% of the total reaction mixture, and its relative amount remained constant during the course of the reaction. The formation of this isomer is due to the contamination of the thionyl chloride by sulfuryl chloride which gives some non-selective chlorination of o-formotoluidide. It is merely carried along in the reaction as an impurity in the o-tolylisocyanide di-chloride. After conversion of the o-formotoluidide and the contaminants 4- and 6-chloro-o-formotoluidide to their respective isocyanide dichlorides, further chlorination by addition of sulfuryl chloride is restricted to forming 4-chloro-o-tolylisocyanide dichloride from o-tolylisocyanide dichloride.

EXAMPLE 2

4-Chloro-o-tolylisocyanide Dichloride

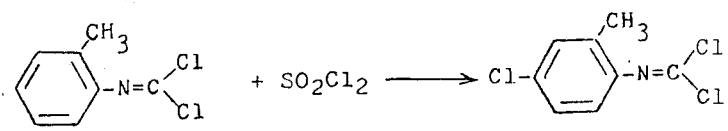

If Example 1 is repeated, but starting with pure o-tolylisocyanide dichloride, there will result isomerically pure 4-chloro-o-tolylisocyanide dichloride. Similarly, 4-chloro-2-n-butylphenylisocyanide dichloride, 4-chloro-2-i-propylphenylisocyanide dichloride, 4-chloro-2-sec-butyl-phenylisocyanide dichloride, 4-chloro-2-(3-hexyl)phenyliso-cyanide dichloride, and 4-chloro-2-ethylphenylisocyanide di-chloride, are all prepared by the above procedure in isomerically pure form when the appropriate 2-substituted phenylisocyanide dichloride is substituted for o-tolylisocyanide dichloride.

EXAMPLE 3

4-Chloro-o-tolylisocyanide Dichloride

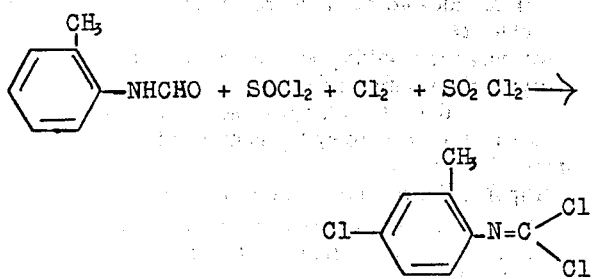

If Example 1 is repeated with initial addition of $Cl_2$ gas to the reaction mixture in place of half of the sulfuryl chloride, essentially identical results are obtained.

EXAMPLE 4

Chlorination of o-Formotoluidide

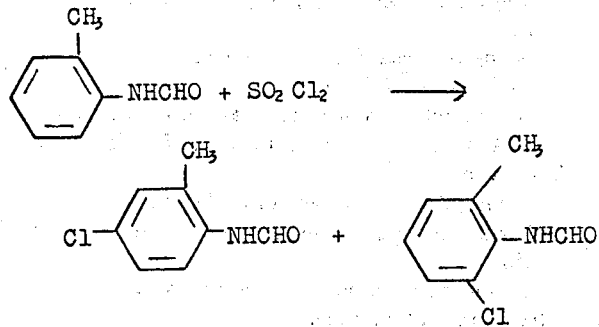

To a solution of one g. (0.0074 mole) of o-formotoluidide in 10 ml. of ethylene dichloride was added 0.72 ml. (0.0081 mole) of sulfuryl chloride. The resulting mixture became thick after a few minutes. It was stirred at room temperature for 3 hrs. The solvent was then removed by evaporation at reduced pressure leaving the product as a solid which gas chromatography (160°, 4 ft. SE 30 on Gaschrome Q, 100–120 mesh) indicated to be 74% 4-chloro-, and 26% 6-chloro-o-formotoluidide.

EXAMPLE 5

4-Chloro-o-tolylisocyanide Dichloride

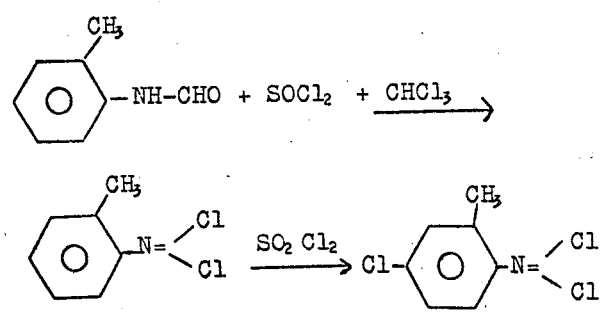

To a solution of o-formotoluidide (6.75 grams, 0.05 mole) dissolved in 100 ml. of chloroform was added dropwise thionyl chloride (7.64 gm, 0.064 mole) at room temperature. The resulting solution was then heated to 60°C. over 1.5 hr. during which time gas evolution was rapid. After cooling the reaction to 5°C., sulfuryl chloride (13.5 gm., 0.1 mole), which was diluted with 40 ml. chloroform, was added dropwise to the reaction solution. The progress of the reaction was monitored by vpc (vapor phase chromatography). A new peak with short retention time (~2 cm, 135°C. 10 ft., SE-30 column, 135°) was observed, but a peak with the retention time of known 4-chloro-2-methylphenylisocyanide dichloride was not present after stirring the reaction at room temperature for 48 hours. The reaction flask was fitted with a distillation head and all of the volatiles were distilled out of the flask. A vpc trace of the residue was the same as previously described for the reaction mixture.

To the above residue was added excess sulfuryl chloride (~50 ml.) and, after stirring the resulting solution overnight at 50°C., the appearance of a peak (vpc) which corresponded to 4-chloro-2-methylphenylisocyanide dichloride, was observed. Further stirring of this solution for 2 days at 50°C. converted the reaction mixture to 90% 4-chloro-2-methylphenylisocyanide dichloride by vpc.

EXAMPLE 6

Preparation of 4-Chloro-o-tolylimino-1,3-dithietane

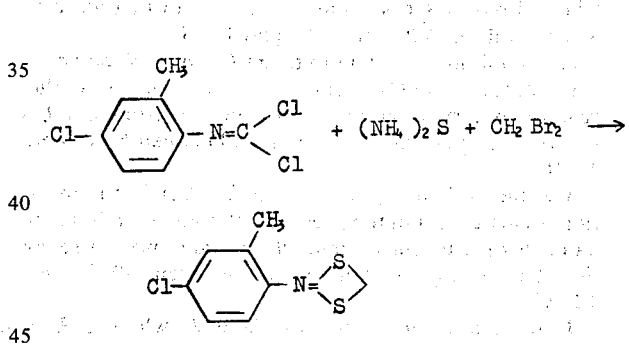

Into an ice water cooled flask containing 20 ml. of dimethylsulfoxide (DMSO) is dropped 16 ml. (0.05 mole) of 21% aqueous $(NH_4)_2S$. To the resulting mixture is added 4.45 grams (0.02 mole) of 4-chloro-o-tolylisocyanide dichloride as prepared in Example 1, above, over 10 minutes with stirring. The temperature is kept below 20°C. by use of the ice water bath. The resulting mixture is stirred at 20°C. for 15 minutes. To this is then added 2.8 ml. (0.04 mole) of methylene bromide dropwise during 15 minutes, keeping the temperature below 20°C. The resultant reaction mixture is stirred at room temperature for 1½ hours. It is then poured into water and extracted with three 30 ml. portions of ether. The ether extract is washed with water and with saturated NaCl, dried, and evaporated giving 6.0 grams of crude yellow product. Analysis of the mixture indicated a 60% yield of dithietane is present. 4.85 Grams of this product is dissolved in 24 ml. of acetone, and stirred with 1.6 ml. of concentrated HCl. The precipitate if filtered off and washed with acetone and ether. The resulting 2.42 grams of white powder is stirred with approximately 20 ml. of ether and 20 ml. of water until all solids have dissolved. The layers are then separated and the organic layer washed with saturated NaCl, dried, and the solvent evaporated at reduced pressure giving 1.94 grams (52.5% yield corrected to the entire sample) of the dithietane as a white solid.

Substituting 2-ethyl-4-dichlorophenylisocyanide dichloride for 4-chloro-o-tolylisocyanide dichloride in the above procedure, yields 2-ethyl-4-dichlorophenylimino-1,3-dithietane.

We claim:

1. A method for the preparation of compounds having the formula:

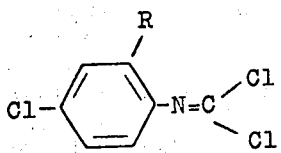

wherein R represents alkyl $C_1$–$C_6$, including straight chain alkyl, branched chain alkyl and cycloalkyl comprising:

reacting an isomerically pure compound having the formula:

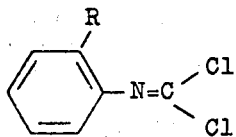

where R is as described above, with a chlorine source at a temperature between 20°C. and 150°C.

2. A method according to claim 1, wherein the chlorine source is sulfuryl chloride or chlorine gas; the reaction is carried out in the absence of solvent and the reaction temperature is maintained between 60°C. and 120°C.

3. A method according to claim 2, wherein the reaction is carried out in the presence of a solvent of chlorinated hydrocarbons or thionyl chloride and the reaction temperature is maintained between 60°C. and 120°C.

4. A method according to claim 2, wherein R is methyl.

5. A method according to claim 3, wherein R is methyl.

6. A method according to claim 1 with the additional steps of
stripping the reaction mixture of solvent,
diluting the reaction mixture with an inert chlorinated hydrocarbon solvent,
washing the resulting solution with water,
drying the solution and
stripping the solvent to give the purified product.

7. A method according to claim 2 with the additional steps of
stripping the reaction mixture of solvent,
diluting the reaction mixture with methylene chloride, chloroform, dichloroethane or carbon tetrachloride,
washing the resulting solution with water,
drying the solution and
stripping the solvent to give the purified product.

8. A method according to claim 3 with the additional steps of
stripping the reaction mixture of solvent,
diluting the reaction mixture with methylene chloride, chloroform dichloroethane or carbon tetrachloride,
washing the resulting solution with water,
drying the solution and
stripping the solvent to give the purified product.

9. A method according to claim 4 with the additional steps of
stripping the reaction mixture of solvent,
diluting the reaction mixture with methylene chloride,
washing the resulting solution with water,
drying the solution and
stripping the solvent to give the purified product.

10. A method according to claim 5 with the additional steps of
stripping the reaction mixture of solvent,
diluting the reaction mixture with methylene chloride,
washing the resulting solution with water,
drying the solution and
stripping the solvent to give the purified product.

* * * * *